United States Patent
Lv et al.

(10) Patent No.: US 9,878,969 B2
(45) Date of Patent: Jan. 30, 2018

(54) PROCESS FOR THE PREPARATION OF 1,3,3,3-TETRAFLUOROPROPENE

(71) Applicant: XI'AN MODERN CHEMISTRY RESEARCH INSTITUTE, Xi'an, Shaanxi (CN)

(72) Inventors: Jian Lv, Shaanxi (CN); Hui Ma, Shaanxi (CN); Yujie Gu, Shaanxi (CN); Bo Wang, Shaanxi (CN); Yue Qin, Shaanxi (CN); Zhenhua Zhang, Shaanxi (CN); Zhijun Hao, Shaanxi (CN); Chunying Li, Shaanxi (CN); Fengxian Li, Shaanxi (CN); Jing Lv, Shaanxi (CN); Yanbo Bai, Shaanxi (CN)

(73) Assignee: Xi'an Modern Chemistry Research Institute, Xi'an (CN)

( * ) Notice: Subject to any disclaimer, the term of this patent is extended or adjusted under 35 U.S.C. 154(b) by 0 days.

(21) Appl. No.: 15/535,220

(22) PCT Filed: Feb. 5, 2015

(86) PCT No.: PCT/CN2015/072303
§ 371 (c)(1),
(2) Date: Jun. 12, 2017

(87) PCT Pub. No.: WO2016/090743
PCT Pub. Date: Jun. 16, 2016

(65) Prior Publication Data
US 2017/0342003 A1     Nov. 30, 2017

(30) Foreign Application Priority Data
Dec. 13, 2014    (CN) .................. 2014 1 07724593

(51) Int. Cl.
| | | |
|---|---|---|
| *C07C 17/20* | (2006.01) | |
| *C07C 21/18* | (2006.01) | |
| *C07C 17/358* | (2006.01) | |
| *B01J 23/00* | (2006.01) | |

(52) U.S. Cl.
CPC ............ *C07C 17/20* (2013.01); *C07C 17/358* (2013.01); *C07C 21/18* (2013.01); *B01D 2255/2045* (2013.01); *B01D 2255/2047* (2013.01); *B01D 2255/2092* (2013.01); *B01D 2255/20715* (2013.01); *B01D 2255/20723* (2013.01); *B01D 2255/20746* (2013.01); *B01D 2255/20753* (2013.01); *B01D 2255/20761* (2013.01); *B01J 23/00* (2013.01)

(58) Field of Classification Search
CPC ..... C07C 17/206; C07C 17/278; C07C 19/01; C07C 19/10; C07C 17/23; C07C 21/04; C07C 17/25; B01J 27/12; B01J 21/04; B01J 27/128; B01J 27/135; B01J 27/138; B01J 37/0201; B01J 27/122; B01J 23/898
See application file for complete search history.

(56) References Cited

U.S. PATENT DOCUMENTS 8,829,254 B2 * 9/2014 Nair ...................... C07C 17/206
570/156

* cited by examiner

*Primary Examiner* — Jafar Parsa
(74) *Attorney, Agent, or Firm* — Stites & Harbison, PLLC; David W. Nagle, Jr.; Terry L. Wright

(57) ABSTRACT

Disclosed is a process for the preparation of 1,3,3,3-tetrafluoropropene, comprising: (a) a compound having the formula $CF_{3-x}Cl_xCHClCHF_{2-y}Cl_y$ and in the presence of a compound catalyst, undergoes, through n serially-connected reactors, gas-phase fluorination with hydrogen fluoride, producing 1,2,3-trichloro-1,1,3-trifluoropropane, and 1,2-dichloro-1,1,3,3-tetrafluoropropane; in said formula, x=1, 2 or 3; y=1 or 2, and $3 \leq x+y \leq 5$; (b) 1,2,3-trichloro-1,1,3-trifluoropropane, and 1,2-dichloro-1,1,3,3-tetrafluoropropane undergo, in the presence of a dehalogenation catalyst, gas-phase dehalogenation with hydrogen, producing 3-chloro-1,3,3-trifluoropropene, and 1,1,3,3-tetrafluoropropene; (c) 3-chloro-1,3,3-trifluoropropene and 1,1,3,3-tetrafluoropropene undergo, in the presence of a fluorination catalyst, gas-phase fluorination with hydrogen fluoride, producing 1,3,3,3-tetrafluoropropene. The present invention is primarily used to produce 1,3,3,3-tetrafluoropropene.

11 Claims, 3 Drawing Sheets

PROCESS FOR THE PREPARATION OF 1,3,3,3-TETRAFLUOROPROPENE

TECHNICAL FIELD

The present invention relates to a process for the preparation of hydrofluoroolefins, and more particularly to a process for the preparation of 1,3,3,3-tetrafluoropropene (HFO-1234ze).

BACKGROUND ART

Hydrofluoroolefins (HFOs), as compared with chlorofluorocarbons (CFCs), Hydrochloroflurocarbons (HCFCs) and hydrofluorocarbons (HFCs), do not contain chlorine and do not pose a threat to the Earth's ozone layer, meanwhile have low Global Warming Potential, which have now become the focus of research in F-chemical industries. 1,3,3,3-tetrafluoropropene, i.e., HFO-1234ze, as one of hydrofluoroolefins, has an ozone depletion potential of 0, has a Global Warming Potential of 6, and can be used as refrigerants, foaming agents, aerosol propellants, extinguishing agents, heat-transfer media, propellants, gaseous dielectrics, sterilizing agent carriers, monomers of polymers and intermediates of medicine and pesticide, and it is widely used in the fields of chemical industry, fire-fighting, aerospace and aviation.

At present, four methods have mainly reported for preparation of HFO-1234ze including fluorine-chlorine exchange, dehydrohalogenation, telomerization and carbene reaction.

There are most reports on the fluorine-chlorine exchange. JP10007604, U.S. Pat. No. 6,472,573 and EP486333 report a method for synthesizing HFO-1234ze by one-step gas phase fluorination with 1-chloro-3,3,3-trifluoropropene (HCFC-1233zd) as raw material, however, the reaction material HCFC-1233zd of the method is expensive and difficult to obtain, furthermore, the transport of the raw material is also inconvenient; the catalysts are chromium-containing catalysts, these chromium-containing compounds and catalyst will cause damage to the human digestive tract and kidney, especially the high-valence chromium has a strong carcinogenic effect, and is unfriendly to people and the environment in the processes of production and use, and will cause serious harm; CN200810000765.X reports a method for preparing HFO-1234ze by gas phase fluorination with 1,1,1,3,3-pentachloropropane (HCC-240fa) as raw material, however, the selectivity of the HFO-1234ze in the method is low, and is only about 50%. US2006030744 reports a method for synthesizing HFO-1234ze using 3,3,3-trifluoropropene (HFO-1243) as raw material, however, the raw material of the method is expensive, the route is complicated, and the addition reaction process is difficult to control.

With respect to dehydrohalogenation, U.S. Pat. No. 7,592,494, EP2014637, EP0974571, Chinese Patent No. CN101265155, Chinese Patent No. CN101466656 and Japanese Patent No. JP10007605 respectively report a method for synthesizing HFO-1234ze using 1,1,1,3,3-pentafluoropropane (HFC-245fa) as raw material, however, the reaction raw material HFC-245fa is expensive. U.S. Pat. No. US20090278075 reports a method for preparing HFO-1234ze and HFO-1234yf with 1,1,1,2,3-pentafluoropropane (HFC-245eb) as raw material, however, the selectivity of the HFO-1234ze in the method is low.

With respect to telomerization, US20050245773 and US20050245774 report that HFO-1234ze is obtained by continuous fluorination after telomerization with halogenated methane and halogenated ethylene as raw materials, however, the route of such a synthesis method is complicated, the catalyst is expensive and easy to coking and deactivation, both the raw material conversion and the selectively of target product are low.

With respect to the process for the preparation of carbene reaction, US20050245774 reports that HFO-1234ze is produced by high temperature reaction of difluorocarbene and vinylidene fluoride monomers in the same reactor at a temperature of above the cracking temperature of the difluorocarbene precursor, the reaction temperature of the synthesis method is high, the yield is low, and the reaction condition is harsh, and there is no industrial application value.

Although there are many methods disclosed presently for preparing HFO-1234ze, they have the deficiencies such as: the raw materials are expensive and difficult to obtain, the catalyst is unfriendly to the environment, and the reaction condition is harsh and the like. Thus, there is a need of a continuous improvement and more efficient preparation methods.

SUMMARY OF THE INVENTION

The purpose of the present invention is to overcome the shortcomings in the prior art and to provide a process for the preparation of 1,3,3,3-tetrafluoropropene (HFO-1234ze), in which the raw materials are cheap and readily available, the catalysts are environmentally friendly, and the reaction conditions are mild.

To achieve the purpose of the present invention, the present invention provides a process for the preparation of 1,3,3,3-tetrafluoropropene, comprising the following steps:

(a) a compound having the general formula of $CF_{3-x}Cl_xCHClCHF_{2-y}Cl_y$ undergoes gas-phase fluorination with hydrogen fluoride in the presence of a compound catalyst through n serially-connected reactors to produce 1,2,3-trichloro-1,1,3-trifluoropropane and 1,2-dichloro-1,1,3,3-tetrafluoropropane; wherein in the compound formula, x=1, 2 or 3; y=1 or 2, and $3 \leq x+y \leq 5$;

(b) 1,2,3-trichloro-1,1,3-trifluoropropane and 1,2-dichloro-1,1,3,3-tetrafluoropropane undergo gas-phase dehalogenation with hydrogen gas in the presence of a dehalogenation catalyst to produce 3-chloro-1,3,3-trifluoropropene, and 1,1,3,3-tetrafluoropropene; and (c) 3-chloro-1,3,3-trifluoropropene and 1,1,3,3-tetrafluoropropene undergo gas-phase fluorination with hydrogen fluoride in the presence of a fluorination catalyst to produce 1,3,3,3-tetrafluoropropene.

The compound having the formula $CF_{3-x}Cl_xCHClCHF_{2-y}Cl_y$ in step (a) is selected from the group consisting of $CCl_3CHClCHCl_2$, $CFCl_2CHClCHCl_2$, $CF_2ClCHClCHCl_2$, $CCl_3CHClCHFCl$ and $CFCl_2CHClCHFCl$.

The compound having the formula $CF_{3-x}Cl_xCHClCHF_{2-y}Cl_y$ in step (a) is $CCl_3CHClCHCl_2$.

The fluorination catalyst in step (a) is a Mn-A-B—C compound catalyst, wherein A is a Group VIII element, B is a high-field-strength element, C is an alkaline-earth metal element, and the molar ratio of Mn, A, B and C is (0.3-2):(0.6-5):(0.1-1):(2-9).

In the Mn-A-B—C compound catalyst in step (a), A is one or a combination of two or more of Ni, Fe and Co, B is one or a combination of two or more of Zr, Y and La, and C is one of Mg, Ca and Ba; and the molar ratio of Mn, A, B and C is (0.6-1):(2-4):(0.4-1):(4-7).

The fluorination catalyst in step (a) is Mn—Ni—Zr—Ca compound catalyst, wherein, the molar ratio of Mn, Ni, Zr and Ca is 0.6:3:0.4:6; the process for the preparation of the catalyst comprises the following steps: a mixed solution of soluble salts of the three metals Mn, Ni and Zr is reacted with the precipitant in proportion, the pH is controlled at 7.5 to 9.5, stirring, precipitating, filtering and drying are conducted, and then an oxide, hydroxide or carbonate of Ca is well mixed therewith the, and then staged calcination is performed at 200° C. to 500° C. under a condition of no less than three temperature gradients, and finally activation treatment is carried out with hydrogen fluoride at 200° C. to 380° C. to obtain the catalyst.

The n serially-connected reactors in step (a) are two serially-connected reactors arranged in series in the flowing direction of the raw material and charged with the same catalyst, which have sequentially increased reaction temperatures.

The reaction conditions of the primary reactor in the two serially-connected reactors in step (a) are as follows: the reaction temperature of the primary reactor is 200° C. to 240° C., the molar ratio of hydrogen fluoride to $CCl_3CHClCHCl_2$ is (5-20):1, and the reaction contact time is 0.5 to 20 seconds; and the reaction conditions of the secondary reactor are as follows: the reaction temperature of the secondary reactor is 280° C. to 320° C., the molar ratio of hydrogen fluoride to the organics in the primary reactor product is (10-20):1, and the reaction contact time is 5 to 30 seconds.

The dechlorination catalyst in step (b) is a Cu—V—Mg—F catalyst, wherein, the molar ratio of Cu, V and Mg is (2-4):(1-2):(4-7); the reaction conditions of gas phase dechlorination are as follows: the reaction temperature is 200° C. to 320° C. tem, the molar ratio of hydrogen to the total of 1,2,3-trichloro-1,1,3-trifluoropropane and 1,2-dichloro-1,1,3,3-tetrafluoropropane is (0-1):1, the contact time is 1 to 30 seconds.

The fluorination catalyst in step (c) is a Al—Co—Zn—F catalyst, wherein, the molar ratio of Al, Co and Zn is (6-8):(1-2):(1-2), and the gas phase fluorination reaction conditions are as follows: the reaction temperature is 120° C. to 240° C., the molar ratio of hydrogen fluoride to the total of 3-chloro-1,3,3-trifluoropropene and 1,1,3,3-tetrafluoropropene is (5-20):1, and the contact time is 0.1 to 20 seconds.

The advantages of the present invention as compared with the prior art are as follows: the present invention provides an efficient process for the preparation of HFO-1234ze, meanwhile its raw material is cheap and readily available, and can be obtained by the reaction of the cheap and commercially available halogenated methane and halogenated ethylene; the catalyst does not involve chromium-containing compounds, which is friendly to human and environment; the reaction conditions are mild, the operation is simple, the gas phase continuous reaction is adopted, and the gas phase reaction temperature is no more than 320° C.

BEST MODE OF THE PRESENT APPLICATION

Figure 1:
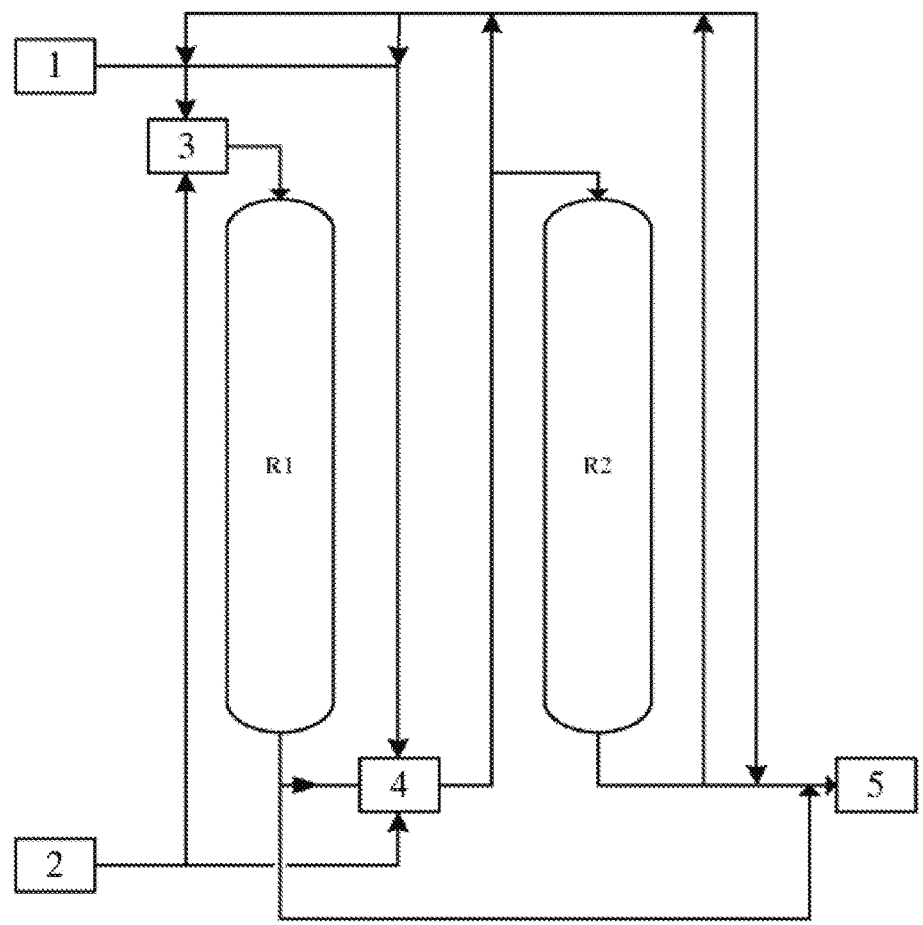
FIG. 1 is a schematic flow of step (a) of the present invention. R1 is a primary reactor, R2 is a secondary reactor, 1 is a reaction feedstock, 2 is hydrogen fluoride, 3 is a static mixer, 4 is a static mixer or heat exchanger or phase separator or a combination thereof, and 5 is a product separation section.

In the present invention, 1,3,3,3-tetrafluoropropene (HFO-1234ze) is generated with a compound having the formula $CF_{3-x}Cl_xCHClCHF_{2-y}Cl_y$ as the starting material by three-steps of reactions including gas phase fluorination, dehalogenation and gas phase fluorination. The reaction scheme is as follows:

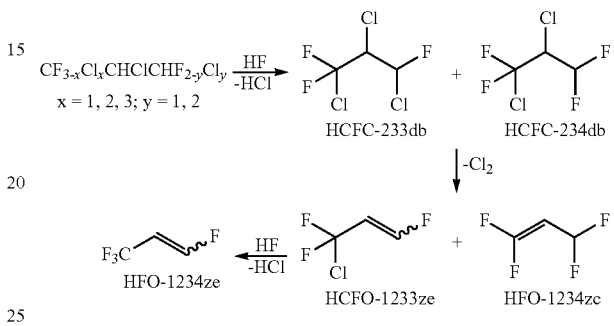

The process for the preparation of HFO-1234ze of the present invention comprises the following steps:

(a) a compound having the general formula of $CF_{3-x}Cl_xCHClCHF_{2-y}Cl_y$ undergoes gas-phase fluorination with hydrogen fluoride in the presence of a compound catalyst through n serially-connected reactors to produce 1,2,3-trichloro-1,1,3-trifluoropropane, and 1,2-dichloro-1,1,3,3-tetrafluoropropane; wherein in the compound formula, x=1, 2 or 3; y=1 or 2, and 3≤x+y≤5;

(b) 1,2,3-trichloro-1,1,3-trifluoropropane (HCFC-233db) and 1,2-dichloro-1,1,3,3-tetrafluoropropane (HCFC-234db) undergo gas-phase dehalogenation with hydrogen gas in the presence of a dehalogenation catalyst to produce 3-chloro-1,3,3-trifluoropropene and 1,1,3,3-tetrafluoropropene; and (c) 3-chloro-1,3,3-trifluoropropene (HCFO-1233ze) and 1,1,3,3-tetrafluoropropene (HFO-1234zc) undergo gas-phase fluorination with hydrogen fluoride in the presence of a fluorination catalyst to produce 1,3,3,3-tetrafluoropropene.

The compound having the formula $CF_{3-x}Cl_xCHClCHF_{2-y}Cl_y$ in step (a) of the present invention is selected from the group consisting of $CCl_3CHClCHCl_2$, $CFCl_2CHClCHCl_2$, $CF_2ClCHClCHCl_2$, $CCl_3CHClCHFCl$, $CFCl_2CHClCHFCl$, $CCl_3CHClCHF_2$ and $CFCl_2CHClCHF$, preferably $CCl_3CHClCHCl_2$, $CCl_3CHClCHFCl$ and $CCl_3CHClCHF_2$, and more preferably $CCl_3CHClCHCl_2$, and suitable reaction material further comprises $CCl_3CHClCHF_2$ and $CFCl_2CHClCHF_2$, accordingly, the generated products under the reaction conditions of step (a) are 1,2-dichloro-1,1,3,3-tetrafluoropropane and 2-chloro-1,1,1,3,3-pentafluoropropane. These reaction starting materials can be prepared by polymerization of cheap and commercially available halogenated methane and halogenated ethylene by a variety of methods, for example, 1,1,1,2,3,3-hexachloropropane can be prepared from trichlorethylene and chloroform in the presence of aluminum trichloride and can also be prepared by reacting 1,2-dichloroethylene and carbon tetrachloride under the presence of catalyst.

The n serially-connected reactors in step (a) of the present invention are n serially-connected reactors arranged in series in the flowing direction of the raw material and charged with the same catalyst, which have sequentially increased reaction temperatures; a static mixer, a heat exchanger, a phase separator, a buffer tank, or other simple separation devices can be installed between the serially-connected reactors according to the requirements to promote the removal and separation of hydrogen chloride or to improve the reaction effect; the gas inlet of the static mixer is connected with the hydrogen fluoride replenishment pipeline, the liquid inlet is connected with the liquid material outlet pipeline of the adjacent superior reactor, and the outlet is connected with the inlet of the adjacent lower reactor; the products of each reactor can selectively enter into the subsequent separation section and/or into at least one of the remaining reactors, wherein, n=2; the conversion rate and product distribution of each reactor are mainly controlled by the reaction temperature, residence time and materials ratio, in the primary reactor, the reaction temperature is 200° C. to 240° C., the molar ratio of HF to $CCl_3CHClCHCl_2$ is (5-30):1, preferably (10-20):1, and the product stream thereof mainly comprises the reaction-generated $CFCl_2CHClCHCl_2$, $CF_2ClCHClClCl_2$, HCl and unreacted HF, the product stream of the primary reactor can be directly introduced into the secondary reactor or be introduced into the second reaction reactor after the generated hydrogen chloride is removed; in the secondary reactor, the reaction temperature is 280° C. to 320° C., the molar ratio of HF to the organic phase in the primary reactor product is (10-20):1, and the product stream thereof mainly comprises $CF_2ClCHClCHFCl$, $CF_2ClCHClCHF_2$, HCl and unreacted HF. The reaction contact times of the two reactors are controlled and adjusted according to the selectivity of the product distribution with the range of 0.5 to 60 seconds; the contact time of the primary reactor is preferably 0.5 to 20 seconds, more preferably 5 to 10 seconds; the contact time of the secondary reactor is preferably 5 to 30 seconds, more preferably 10 to 20 seconds. After the catalyst in one of the reactors in the serially-connected reactor is inactivated, the reactor can be isolated from the apparatus to carry out the catalyst regeneration operation.

The compound catalyst in step (a) of the present invention is Mn-A-B—C compound catalyst, wherein, A is a group VIII element, B is a high-field-strength element, i.e., an element having a relatively high ionic valence, a relatively small radius, and a relatively high ion field strength, including lanthanide such as Sc and Y, Th, U, Pb, Zr, Hf, Ti, Nb, Ta and the like, and C is an alkaline-earth metal element; A is preferably one or a combination of two or more of Ni, Fe and Co, B is preferably one or a combination of two or more of Zr, Y and La, and C is preferably one of Mg, Ca and Ba; and the molar ratio of Mn, A, B and C is (0.3-2):(0.6-5):(0.1-1):(2-9), preferably (0.6-1):(2-4):(0.4-1):(4-7), and more preferably 0.6:3:0.4:6.

The weight percentage contents of $CF_2ClCHClCHFCl$ and $CF_2ClCHClCHF_2$ in the products of step (a) of the present invention can be adjusted by the catalyst, reaction temperature, molar ratio and contact time according to the requirements, wherein, the weight percentage content of $CF_2ClCHClCHFCl$ is about 80% to 99% and the weight percentage content of $CF_2ClCHClCHF_2$ is about 0.5% to 18%.

The reaction in step (a) of the present invention may be carried out in any reactor suitable for the gas phase fluorination reaction and it is a selective gas phase fluorination reaction in the presence of a compound catalyst. The type of fluorination reactor of step (a) is not critical, while tubular reactor, fluidized bed reactor and the like can be used. In addition, an adiabatic reactor or isothermal reactor is also available.

The dehalogenation reaction in step (b) of the present invention is a gas phase dehalogenation reaction in the presence of a dehalogenation catalyst, the dehalogenation catalyst is a Cu—V—Mg—F catalyst, and the molar ratio of Cu, V and Mg is (2-4):(1-2):(4-7), preferably (3-4):(1-2):(4-6), more preferably 4:1:5, the suitable process for the preparation of the catalyst comprises the preparation methods of catalyst such as impregnation method, coprecipitation method, blending method, sol-gel method and the like. Of course, the dehalogenation reaction may also be a liquid phase dehalogenation reaction under the effect of HCFC-233db, HCFC-234db and reducing agent in a protonic solvent, wherein the protonic solvent includes methanol, ethanol, acetic acid or ethylene glycol, and it certainly also can be tert-butanol, formic acid, acetic anhydride, glycerol or diethylene glycol, meanwhile other common protonic solvents are also suitable for the step, such as propylene glycol, polyethylene glycol 200 and polyhydric alcohol in which the hydroxyl groups are not fully protected; the reducing agent is Mg, Al, Zn or Fe, or Ag and Fe bimetallic reducing system, and may also be a composition of Cu, Ag, Ni and Fe, a composition of Cu and Fe, a composition of Cu and Al, a composition of Pd and Fe, and combinations thereof.

The gas phase dehalogenation reaction in step (b) of the present invention can achieve the conversion to HCFO-1233yf and HFO-1234zc at a relatively high conversion rate and high selectivity at a relatively low reaction temperature of 200° C. to 300° C. The molar ratio of hydrogen to the total of HCFC-233db and HCFC-234db in the gas phase dehalogenation reaction is a key factor affecting the reaction. When the excess hydrogen is introduced, although the reaction can achieve complete conversion, the selectivity of the target product is significantly reduced, the suitable molar ratio of hydrogen to the total of HCFC-233db and HCFC-234db is (0-1):1, preferably (0.1-0.8):1, more preferably (0.2-0.5):1. Hydrogen may be introduced intermittently, semi-continuously or continuously. The contact time For the gas phase dehalogenation reaction is selected in the range of 1 to 60 seconds according to the amount of the introduced hydrogen, preferably 5 to 30 seconds.

The fluorination catalyst in the step (c) of the present invention is an Al—Co—Zn—F catalyst, and the molar ratio of Al, Co and Zn, which is an important factor affecting the fluorination reaction, is (6-8):(1-2):(1-2), preferably 7:2:1, the suitable process for the preparation of the catalyst comprises impregnation method, coprecipitation method, blending method and sol-gel method.

The fluorination reaction in step (c) of the present invention also includes the isomerization reaction of HFO-1234zc, which can mainly produce trans-HFO-1234ze by the isomerization reaction under Al—Co—Zn—F catalyst, or can produce HFO-1234ze by the reaction of 1,2-position addition and subsequent reaction of 2,3-position elimination with HF.

The control of the reaction temperature in the step (c) of the present invention is one of the key factors in the gas phase fluorination catalytic reaction, and the reaction temperature is in a range of 120° C. to 240° C., preferably 150° C. to 180° C. When the temperature is too high, the polymeric by-products are increased, causing a serious carbon deposition of the catalyst, resulting in catalyst deactivation and life reduction. When the temperature is too low, the reaction conversion rate will be disadvantageously reduced. In particular, when the reaction is carried out at a temperature higher than 260° C., carbides are adhered to or deposited on the reaction tube wall or filler, and the inside of the reactor is gradually blocked. With respect to this situation, it is possible to relieve or eliminate the situation by introducing a certain amount of $N_2$ to dilute the reaction material, and it is also possible to remove the carbides residue in the reaction tube by suspending the reaction and introducing oxygen or air into the reactor.

In the embodiments of steps (a), (b) and (c) of the present invention, preferably the process stream is passed down through the catalyst bed layer. The catalyst is preferably dried, preheated and activated prior to each use. It may also be advantageous to periodically regenerate the catalyst in situ in the reactor after use for a long time. The pretreatments of the fluorination catalyst in steps (a) and (c) can be carried out by heating the catalyst to about 200° C. to about 380° C. in nitrogen or other inert gas stream, and then the catalyst can be treated and activated with a hydrogen fluoride stream that is diluted with highly excessive nitrogen to obtain high catalyst activity. The dechlorination catalyst in step (b) further needs to be activated in a hydrogen atmosphere. The regeneration of the catalysts can be carried out under the following conditions: the air or the air diluted with nitrogen is allowed to pass through the catalyst at a temperature of about 100° C. to about 380° C., preferably about 150° C. to about 365° C., for about 8 hours to about 3 days, depending on the size of the reactor.

The present invention will now be described in further detail with reference to the specific examples.

Analytical Instruments: Haixin Gas Chromatograph GC-930, Agilent 30m DB-5 (50 m×0.32 mm) capillary chromatographic column; ITQ 700 (ion trap): Thermofisher scientific, Agilent GASPRO (60 m×0.25 mm) capillary chromatographic column.

Chromatographic conditions: an initial column temperature of 40° C., keeping for 5 min, heating at a rate of 10° C./min to 180° C., and keeping for 3 min; a vaporizing chamber temperature of 220° C., and a split ratio of 50.

The conditions for ion trap mass spectrometry: a filament emission current of 70 A; a mass scanning range of 10-350 amu; full scan mode, a scan speed of 10 micro-scan/sec; a multiplier voltage of 1556V; a transmission line temperature of 220° C., and helium as carrier gas.

Example 1

Figure 2:
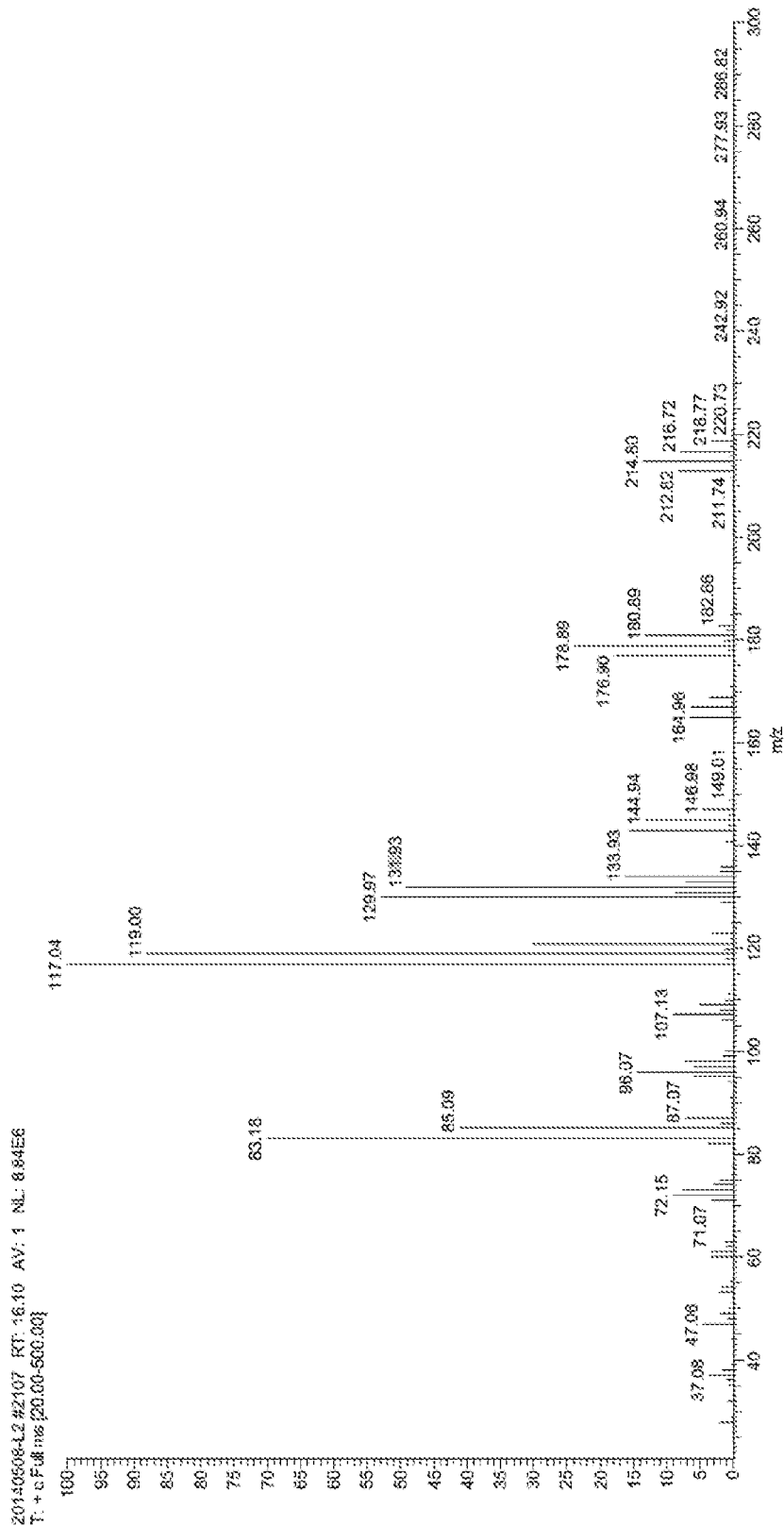
FIG. 2 is a GC-MS chromatogram of the product $CCl_3CHClCHCl_2$.

Trichloropropene (20.0 g, 0.15 mol) and 120 mL of chloroform were successively added into a 250 mL dry three-necked flask equipped with a magnetic stirrer, a thermometer and a coagulation apparatus, and anhydrous aluminum trichloride (2.0 g, 0.015 mol) was added to the reaction solution in three times under constant stirring, and then gradually heating to 60° C. to react for 12 h, the reaction solution was cooled to about 30° C., filtered, and the filtrate was distilled under reduced pressure condition, the fraction in 120° C. to 125° C. was collected under a vacuum degree of 5 kPa to obtain 1,1,1,2,3,3-hexachloropropane (HCC-230da), the conversion was 85.7% and the selectivity was 90.4%. The mass spectrometry results were as follows:

The mass spectrum results shown in FIG. 2 and the peaks assignment thereof are as follows: the substance does not exist molecular ion peak, m/z 213:m/z 215:m/z 217:m/z 219:m/z 221:m/z 223=243:405:270:90:15:1[(M-Cl)$^+$], which is an isotopic peak ratio for the fragment containing five chlorine atoms; m/z 177:m/z 179:m/z 181:m/z 183:m/z 185=81:108:54:12:1[(M-Cl—HCl)$^+$], which is an isotopic peak ratio for the fragment containing four chlorine atoms; m/z 143:m/z 145:m/z 147:m/z 149:=27:27:9:1[(M-3Cl)$^+$], which is an isotopic peak ratio for the fragment containing three chlorine atoms, the loss is reasonable; m/z 130:m/z 132:m/z 134:m/z 136:=27:27:9:1[$C_2HCl_3^+$], m/z 117:m/z 119:m/z 121:m/z 123=27:27:9:1($CCl_3^+$), m/z 83:m/z 85:m/z 87=9:6:1($CHCl_2^+$), m/z 47:m/z 49=3:1($CCl^+$), thus, the compound was 1,1,1,2,3,3-hexachloropropane.

Example 2

The process of step (a) is described as follows:

The reaction material 1 was firstly well mixed with the hydrogen fluoride 2 in the static mixer 3, and then introduced into the primary reactor R1 and the secondary reactor R2 successively. After reacting at the bottom of the primary reactor R1, the mixture was well mixed with hydrogen fluoride by a static mixer 4 (or a phase separator, heat exchanger, separation device or a combination thereof according to the requirements), and then introduced into the secondary reactor R2 to carry out the reaction, then the reaction product was introduced into the separation section 5.

When the catalyst in reactor R1 was inactivated, the reactor R1 was cut out of the system for regeneration. The reaction material 1 was well mixed with the hydrogen fluoride 2 in the static mixer 4, and then introduced into the reactor R2 successively to carry out reaction. When the reactor R1 was regenerated, the order of the raw materials entering into the reaction was R2 and R1. The products were discharged from the bottom of the reactor R1.

The continuous series operation was achieved by adjusting and compensating the reactor reaction temperature and materials proportion or even changing the materials flow through the reactor product distribution of the each reactor so as to generate the products which were introduced into the product separation section 5.

Preparation of the Catalyst:

The manganese acetate, nickel nitrate, zirconium chloride were mixed at a certain proportion to form 2 mol/L aqueous solution, and then the ammonia water with a mass fraction of 15% was dropwise added at 20° C. to 40° C. under constant stirring, the pH was adjusted at about 8.0, reacting for 8 h, filtered, and then dried at 120° C. for 2 h, and well mixed with a certain amount of calcium carbonate, and sequentially calcined as follows: calcining at 200° C. for 1 h, heating at a rate of 5° C./min to 320° C., calcining for 2 h, heating at a rate of 10° C./min to 450° C. and calcining for 4 h. Finally, the product was activated with hydrogen fluoride at 200° C. to 380° C. for about 36 h to obtain the catalyst.

To a nickel tube fixed bed tube reactor having an inner diameter of 38 mm, 50 ml of the Mn—Ni—Zr—Ca compound catalyst was charged, wherein the molar ratio of Mn, Ni, Zr and Ca was 0.6:3:0.4:6, and the catalyst was dried, and then HF and $CCl_3CHClCHCl_2$ (HCC-230da) were introduced into the primary reactor R1 at 220° C., the molar ratio of HF and $CCl_3CHClCHCl_2$ was controlled to 10:1, the contact time was controlled to 10 s, and the product stream thereof, i.e., the stream mainly comprises the reaction-generated $CFCl_2CHClCHCl_2$, $CF_2ClCHClClCl_2$, HCl and unreacted HF, and the HF added additionally were introduced into the secondary reactor R2, the temperature of the secondary reactor was 300° C., the molar ratio of HF to the total of the organics in the primary reactor product was 15:1, and the contact time was 20 seconds. All reactions were carried out under the atmospheric pressure (ordinary pressure). The reaction products were subjected to washing with water and alkali to remove HCl and HF, and were analyzed by gas chromatography and mass spectrometry. While $CF_2ClCHClCHFCl$ (HCFC-233db) and $CF_2ClCHClCHF_2$ (HCFC-234db) were generated, a small amount of 1,2-dichloro-3,3,3-trifluoropropene (HCFO-1223xd) was generated, the results were shown in Table 1.

Examples 3-5

The reactions in Examples 3 to 5 were carried out in the same manner as that in Example 2, the differences were that, the reaction temperature of the primary reactor (R1) and the secondary reactor (R2) in Example 2 were 220° C. and 300° C. respectively, while the reaction temperature and reaction results of R1 and R2 in Examples 3 to 5 were shown in Table 1.

TABLE 1

| Examples | Reaction temperatures (° C.) | | Conversion rates of 230da (%) | Selectivity (%) | | | |
|---|---|---|---|---|---|---|---|
| | R1 | R2 | | R1 | | R2 | |
| | | | | 231da | 232da | 233db | 234db |
| 2 | 220 | 300 | 100 | 23.8 | 74.4 | 92.1 | 2.1 |
| 3 | 220 | 280 | 100 | 23.8 | 74.4 | 96.4 | 1.2 |
| 4 | 200 | 320 | 100 | 35.3 | 63.7 | 87.6 | 3.6 |
| 5 | 240 | 310 | 100 | 19.1 | 87.6 | 90.3 | 2.7 |

Examples 6-8

The reactions in Examples 6 to 8 were carried out in the same manner as that in Example 2, the differences were that, the ratios (molar ratio) of HF to organic materials in R1 and R2 in Example 2 were 10:1 and 15:1 respectively, and the contact time in R1 and R2 were 10 s and 20 s, respectively, while the ratios (molar ratio) of HF to organic materials, contact time and reaction results in Examples 6 to 8 were shown in Table 2, wherein the conversion rates of 230 da were 100%.

TABLE 2

| Examples | Materials proportions | | Contact times (s) | | Selectivity (%) | | | |
|---|---|---|---|---|---|---|---|---|
| | R1 | R2 | R1 | R2 | R1 | | R2 | |
| | | | | | 231da | 232da | 233db | 234db |
| 6 | 5:1 | 10:1 | 1 | 5 | 65.4 | 34.1 | 98.0 | 0.8 |
| 7 | 10:1 | 20:1 | 5 | 20 | 41.0 | 57.6 | 93.4 | 1.9 |
| 8 | 20:1 | 15:1 | 20 | 30 | 20.8 | 71.5 | 85.4 | 4.5 |

Examples 9-12

The reactions in Examples 9 to 12 were carried out in the same manner as that in Example 2, the differences were that, the molar ratio of Mn, Ni, Zr and Ca in the catalyst of Example 2 was 0.6:3:0.4:6, while the molar ratio thereof in Examples 9 to 12 were 0.3:4:0.7:5, 0.6:1:0.4:8, 1:2:1:6, and 2:5:0.5:2.5 respectively, the reaction results were shown in Table 3.

TABLE 3

| Examples | Molar ratios of Mn, Ni, Zr and Ca | Conversion rates of 230da (%) | Selectivity (%) | | | |
|---|---|---|---|---|---|---|
| | | | R1 | | R2 | |
| | | | 231da | 232da | 233db | 234db |
| 9 | 0.3:4:0.7:5 | 100 | 18.1 | 73.3 | 89.3 | 4.0 |
| 10 | 0.6:1:0.4:8 | 100 | 24.7 | 73.9 | 97.8 | 1.1 |
| 11 | 1:2:1:6 | 100 | 30.2 | 64.5 | 94.9 | 1.5 |
| 12 | 2:5:0.5:2.5 | 100 | 7.6 | 82.1 | 83.2 | 6.3 |

Examples 13-19

The reactions in Examples 13 to 19 were carried out in the same manner as that in Example 2, the differences were that, the catalyst in Example 2 was a Mn—Ni—Zr—Ca compound catalyst, while the catalysts in Examples 13 to 19 were Mn—Ni—La—Ca, Mn—Fe—Zr—Mg, Mn—Fe—La—Mg, Mn—Co—Y—Ca, Mn—Co—Y—Ba, Mn—Ni—Y—Ca, and Mn—Fe—Y—Ca respectively. The reaction results were shown in Table 4.

TABLE 4

| Examples | Catalysts | Conversion rates of 230da (%) | Selectivity (%) | | | |
|---|---|---|---|---|---|---|
| | | | R1 | | R1 | |
| | | | 231da | 232da | 233db | 234db |
| 13 | Mn—Ni—La—Ca | 100 | 22.3 | 76.1 | 93.2 | 2.3 |
| 14 | Mn—Fe—Zr—Mg | 100 | 12.2 | 79.6 | 85.7 | 4.3 |
| 15 | Mn—Fe—La—Mg | 100 | 16.7 | 75.4 | 86.2 | 3.9 |
| 16 | Mn—Co—Y—Ca | 100 | 27.4 | 71.2 | 92.0 | 2.4 |
| 17 | Mn—Co—Y—Ba | 100 | 30.4 | 68.2 | 94.8 | 1.7 |
| 18 | Mn—Ni—Y—Ca | 100 | 38.7 | 58.6 | 95.9 | 1.3 |
| 19 | Mn—Fe—Y—Ca | 100 | 19.5 | 77.7 | 91.3 | 3.5 |

Example 20

The preparation of catalyst: $V_2O_5$ was added to a mixed aqueous solution of Mg $(NO_3)_2 \cdot 6H_2O$ and $Cu(NO_3)_2 \cdot 3H_2O$ at a certain proportion, and the pH was adjusted to about 9 by adding the ammonium bicarbonate with a mass fraction of 10%, after about 5 h, the product was centrifugal separated after washing, then dried at 120° C., and then calcined as follows: calcining at 200° C. for 1 h, heating at a rate of 5° C./min to 300° C., calcining for 2 h, then heating at a rate of 5° C./min to 450° C. and calcining for 4 h. Finally, the product was activated with hydrogen fluoride and hydrogen successively to obtain the catalyst.

To a fixed bed tube reactor having an inner diameter of 38 mm, 50 ml of the Cu—V—Mg—F catalyst in which the molar ratio of Cu, V and Mg was 4:1:5 was charged, $H_2$ was introduced at 280° C. Two hours later, 1,2,3-trichloro-1,1,3-trifluoropropane (HCFC-233db) and 1,2-dichloro-1,1,3,3-tetrafluoropropane (HCFC-234db) (the weight percentage contents thereof were 93.6% and 5.2% respectively) were introduced to carry out the reaction at atmospheric pressure (ordinary pressure), the molar ratio of hydrogen to the total of HCFC-233db and HCFC-234db was controlled to 0.3:1, the contact time was 20 seconds, and the reaction results were analyzed by gas chromatography and mass spectrometry. While 3-chloro-1,3,3-trifluoropropene (HCFO-1233ze) and 1,1,3,3-tetrafluoropropene (HFO-1234zc) were generated, the by-products CF$_2$ClCH$_2$CH$_2$F (HCFC-253fc) appeared. The conversion rate of the dehalogenation reaction was a sum of the conversion rates of HCFC-233db and HCFC-234db. The results were shown in Table 5.

Examples 21-23

The preparation of 3-Chloro-1,3,3-trifluoropropene (HCFO-1233ze) and 1,1,3,3-tetrafluoropropene (HFO-1234zc) in Examples 21 to 23 were carried out in the same manner as that in Example 20, the differences were that, the reaction temperature in Example 20 was 280° C., while the reaction temperatures in Examples 21 to 23 were 200° C., 240° C. and 320° C. respectively, and the reaction results were shown in Table 5.

TABLE 5

| Examples | Reaction temperatures | Conversion rates of dehalogenation reaction (%) | Product distributions (%) | |
|---|---|---|---|---|
| | | | HCFO-1233ze | HFO-1234zc |
| 20 | 280 | 82.9 | 93.7 | 2.2 |
| 21 | 200 | 53.4 | 96.6 | 0.9 |
| 22 | 240 | 77.5 | 95.2 | 1.6 |
| 23 | 320 | 91.3 | 86.3 | 4.3 |

Examples 24-27

The preparation of HCFO-1233ze and HFO-1234zc in Examples 24 to 27 were carried out in the same manner as that in Example 20, the differences were that, the molar ratio of Cu, V and Mg in the catalyst of Example 20 was 4:1:5, while the molar ratios of Cu, V and Mg in the catalysts of Examples 24 to 27 were 2:1:7, 3:1:6 and 3:2:5 respectively, and the reaction results were shown in Table 6.

TABLE 6

| Examples | Molar ratios of Cu, V and Mg | Conversion rates of the dehalogenation reaction (%) | Product distributions (%) | |
|---|---|---|---|---|
| | | | HCFO-1233ze | HFO-1234zc |
| 24 | 2:1:7 | 75.1 | 92.9 | 3.4 |
| 25 | 3:1:6 | 86.5 | 94.7 | 2.7 |
| 26 | 3:2:5 | 100 | 70.2 | 5.2 |

Examples 27-29

The preparation of HCFO-1233ze and HFO-1234zc in Examples 27 to 29 were carried out in the same manner as that in Example 20, the differences were that, the molar ratio of hydrogen to the total of HCFC-233db and HCFC-234db in Example 20 was 0.3:1, while the molar ratios in Examples 27 to 29 were 0.1:1, 0.5:1 and 1:1 respectively, and the reaction results were shown in Table 7.

TABLE 7

| Examples | Molar ratios | Conversion rates of the dehalogenation reaction (%) | Product distributions (%) | |
|---|---|---|---|---|
| | | | HCFO-1233ze | HFO-1234zc |
| 27 | 0.1:1 | 71.7 | 97.6 | 0.6 |
| 28 | 0.5:1 | 86.4 | 94.1 | 3.5 |
| 29 | 1:1 | 93.6 | 80.8 | 4.7 |

Examples 30-32

The preparation of HCFO-1233ze and HFO-1234zc in Examples 30 to 32 were carried out in the same manner as that in Example 20, the differences were that, the contact time in Example 20 was 20 s, while the contact times in Examples 30 to 32 were 5 s, 10 s and 30 s, the results were shown in Table 8.

TABLE 8

| Examples | Contact times (s) | Conversion rates of the dehalogenation reaction (%) | Product distributions (%) | |
|---|---|---|---|---|
| | | | HCFO-1233ze | HFO-1234zc |
| 30 | 5 | 55.8 | 96.6 | 0.9 |
| 31 | 10 | 71.3 | 94.2 | 2.2 |
| 32 | 30 | 78.2 | 92.3 | 3.8 |

Example 33

The reaction was carried out in the same manner as that in Example 20, the differences were that, the reaction materials in Example 20 were 1,2,3-trichloro-1,1,3-trifluoropropane and 1,2-dichloro-1,1,3,3-tetrafluoropropane (the weight percentage contents thereof were 93.6% and 5.2% respectively), while the reaction material of Example 33 was 1,2-dichloro-1,1,3,3-tetrafluoropropane, and the reaction results were as follows: reaction conversion rate was 79.5%, the selectivity of HCFO-1233ze was 69.1%, and the selectivity of HFO-1234zc was 30.0%.

Example 34

The reaction was carried out in the same manner as that in Example 20, the differences were that, the reaction materials in Example 20 were 1,2,3-trichloro-1,1,3-trifluoropropane and 1,2-dichloro-1,1,3,3-tetrafluoropropane (the weight percentage contents thereof were 93.6% and 5.2% respectively), while the reaction material of Example 34 was 1,2,3-trichloro-1,1,3-trifluoropropane, and the reaction results were as follows: reaction conversion rate was 85.1%, and the selectivity of HFO-1234zc was 98.4%.

Example 35

The preparation of catalyst: Al(NO$_3$)$_3$.9H$_2$O, Co(NO$_3$)$_2$.6H$_2$O and Zn(NO$_3$)$_2$.6H$_2$O were accurately weighed according to a certain proportion, then to the mixed aqueous solution thereof, ammonia water with a mass fraction of 10% was dropwise added to adjust the pH at about 7 to 9, after about 6 h, the product was centrifugal separated after washing, then dried at 120° C., and then calcined as follows: calcining at 200° C. for 1 h, heating at a rate of 5° C./min to 300° C., calcining for 2 h, then heating at a rate of 5° C./min to 450° C. and calcining for 4 h. Finally, the product was activated with hydrogen fluoride to obtain the catalyst.

To a fixed bed tube reactor having an inner diameter of 38 mm, 50 ml of the Al—Co—Zn—F catalyst in which the molar ratio of Al, Co and Zn was 7:2:1 was charged, and the catalyst was dried and second activated, after activation was complete, HF, 3-chloro-1,3,3-trifluoropropylene (HCFO-1233ze) and 1,1,3,3-tetrafluoropropene (HFO-1234zc) (the weight percentage contents thereof were 94.1% and 4.6%) were introduced at 150° C. to carry out reaction at the atmospheric pressure (ordinary pressure), the molar ratio of HF to the total of HCFO-1233ze and HFO-1234zc was controlled to 15:1, and the contact time was 15 seconds. The reaction products were subjected to washing with water and alkali to remove HCl and HF, and were analyzed by gas chromatography and mass spectrometry. The conversion rate of the fluorination reaction was a sum of that of HCFO-1233ze and HFO-1234zc, the mass spectrographic analysis results were shown in FIG. 3, and the reaction results were shown in Table 9.

Figure 3:
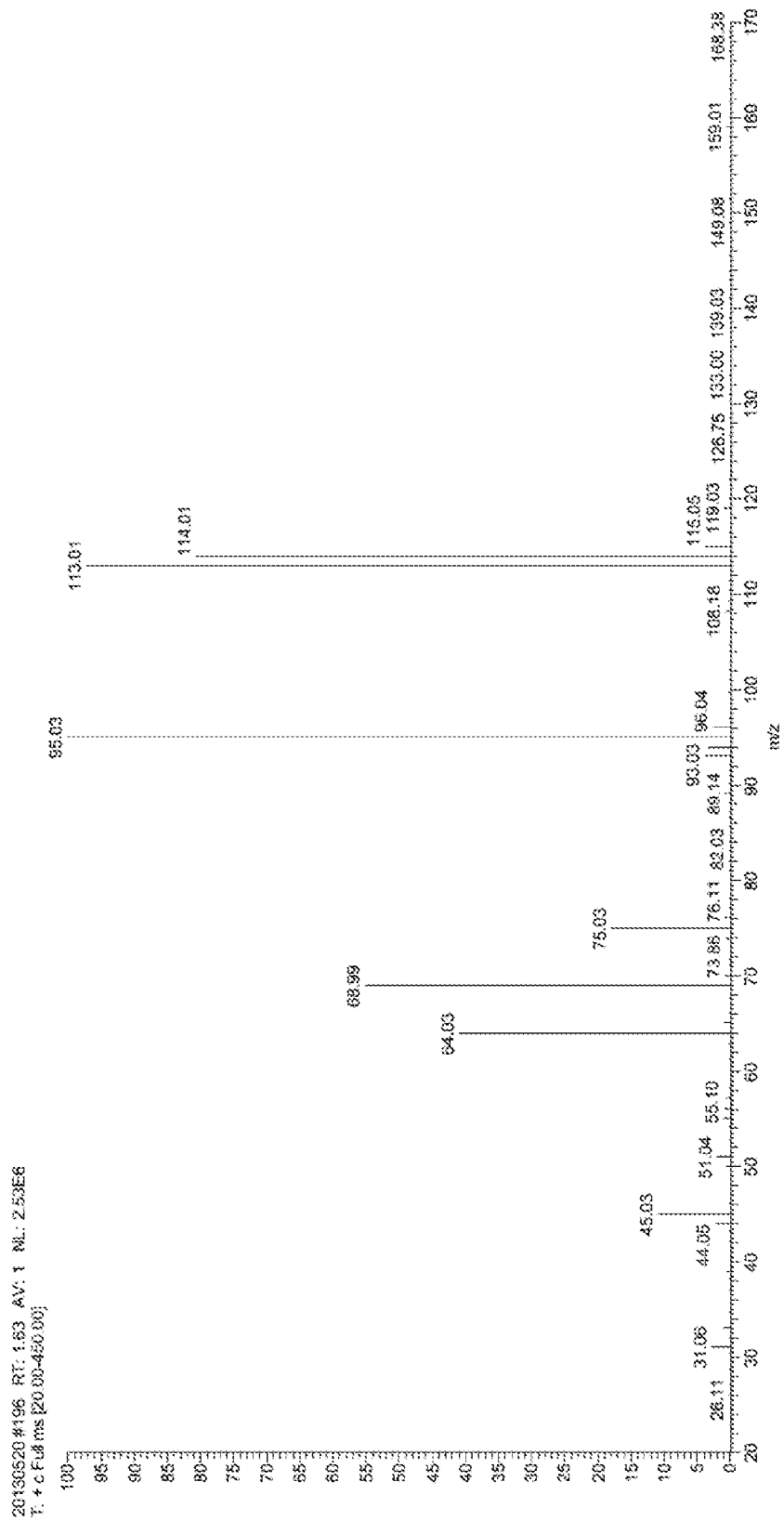
FIG. 3 is a GC-MS chromatogram of the product HFO-1234ze.

Mass spectrum results shown in FIG. 3 and the peaks assignment thereof were as follows: m/z 114($M^+$), m/z 95[$(M-F)^+$], m/z 75($C_3HF_2^+$), m/z 69($CF_3^+$), m/z 64($C_2H_2F_2^+$), m/z 45($C_2H_2F^+$), m/z 44($C_2HF^+$), the loss was reasonable, the compound name was: 1,3,3,3-tetrafluoropropene.

Examples 36-38

The preparation of 1,3,3,3-tetrafluoropropene in Examples 36 to 38 were carried out in the same manner as that in Example 35, the differences were that, the reaction temperature in Example 35 was 150° C., while the reaction temperatures of Examples 36 to 38 were 120° C., 180° C. and 240° C. respectively, and the reaction results were shown in Table 9.

TABLE 9

| Examples | Reaction temperatures | Conversion rates of the fluorination reaction (%) | Selectivity (%) trans-1234ze | cis-1234ze |
|---|---|---|---|---|
| 35 | 150 | 92.8 | 85.1 | 11.2 |
| 36 | 120 | 83.6 | 87.2 | 10.9 |
| 37 | 180 | 97.2 | 81.5 | 13.6 |
| 38 | 240 | 100 | 76.9 | 15.4 |

Examples 39-41

The preparation of 1,3,3,3-tetrafluoropropene in Examples 39 to 41 were carried out in the same manner as that in Example 35, the differences were that, the molar ratio of Al, Co and Zn in the catalyst of Example 35 was 7:2:1, while the molar ratios of thereof in the catalysts in Examples 39 to 41 were 6:2:2, 7:1:2 and 8:1:1 respectively, and the reaction results were shown in Table 10.

TABLE 10

| Examples | Molar ratios of Al, Co and Zn | Conversion rates of the fluorination reaction (%) | Selectivity (%) trans-1234ze | cis-1234ze |
|---|---|---|---|---|
| 39 | 6:2:2 | 88.6 | 86.9 | 11.4 |
| 40 | 7:1:2 | 91.8 | 83.5 | 13.9 |
| 41 | 8:1:1 | 95.4 | 82.3 | 15.6 |

Examples 42-43

The preparation of 1,3,3,3-tetrafluoropropene in Examples 42 to 43 were carried out in the same manner as that in Example 35, the differences were that, the molar ratio of hydrogen fluoride to the total of HCFO-1233ze and HFO-1234zc in Example 35 was 15:1, while the molar ratios thereof in Examples 42 to 43 were 10:1 and 20:1 respectively, and the reaction results were shown in Table 11.

TABLE 11

| Examples | Molar ratios | Conversion rates of the fluorination reaction (%) | Selectivity (%) trans-1234ze | cis-1234ze |
|---|---|---|---|---|
| 42 | 10:1 | 93.1 | 86.4 | 10.9 |
| 43 | 20:1 | 91.7 | 83.3 | 12.5 |

Examples 44-46

The preparation of 1,3,3,3-tetrafluoropropene in Examples 44 to 46 were carried out in the same manner as that in Example 35, the differences were that, the contact time in Example 35 was 15 s, while the contact time in Examples 44 to 46 were 5 s, 10 s and 20 s respectively, the results were shown in Table 12.

TABLE 12

| Examples | Contact times | Conversion rates of the fluorination reaction (%) | Selectivity (%) trans-1234ze | cis-1234ze |
|---|---|---|---|---|
| 44 | 5 | 82.5 | 80.1 | 18.4 |
| 45 | 10 | 90.4 | 83.2 | 13.7 |
| 46 | 20 | 100 | 87.3 | 9.1 |

Example 47

The reaction was carried out in the same manner as that in Example 35, the differences were that, the reaction materials in Example 35 was the mixture of 3-chloro-1,3,3-trifluoropropene and 1,1,3,3-tetrafluoropropene (the weight percentage contents thereof were 94.1% and 4.6%), while the reaction material of Example 47 was 3-chloro-1,3,3-trifluoropropene, and the reaction results were: the reaction conversion rate was 99.6%, and the selectivities of trans-HFO-1234ze and cis-HFO-1234ze were 90.8% and 9.1% respectively.

Example 48

The reaction was carried out in the same manner as that in Example 35, the differences were that, the reaction material in Example 35 was the mixture of 3-chloro-1,3,3-trifluoropropene and 1,1,3,3-tetrafluoropropene (the weight percentage contents thereof were 94.1% and 4.6%), while the reaction material of Example 48 was 1,1,3,3-tetrafluoropropene, and the reaction results were: the reaction conversion rate was 95.4%, and the selectivities of trans-HFO-1234ze and cis-HFO-1234ze were 87.5% and 11.6% respectively.

The foregoing is only a part of the examples of the present invention and not intended to limit the scope of the invention. Any simple changes, equivalent variations and modifications to the above-mentioned examples in accordance with the technical essence of the present invention fall within the scope of the technical solutions of the present invention.

What is claimed is:

1. A process for the preparation of 1,3,3,3-tetrafluoropropene comprising the following steps:
   (a) a compound having the general formula of $CF_{3-x}Cl_xCHClCHF_{2-y}Cl_y$ undergoes gas-phase fluorination with hydrogen fluoride in the presence of a fluorination catalyst through n serially-connected reactors to produce 1,2,3-trichloro-1,1,3-trifluoropropane, and 1,2-dichloro-1,1,3,3-tetrafluoropropane; wherein in the compound formula, x=1, 2 or 3; y=1 or 2, and 3≤x+y≤5;

(b) 1,2,3-trichloro-1,1,3-trifluoropropane and 1,2-dichloro-1,1,3,3-tetrafluoropropane undergo gas-phase dehalogenation with hydrogen in the presence of a dehalogenation catalyst to produce 3-chloro-1,3,3-trifluoropropene and 1,1,3,3-tetrafluoropropene; and (c) 3-chloro-1,3,3-trifluoropropene and 1,1,3,3-tetrafluoropropene undergo gas-phase fluorination with hydrogen fluoride in the presence of a fluorination catalyst to produce 1,3,3,3-tetrafluoropropene.

2. The process for the preparation of 1,3,3,3-tetrafluoropropene according to claim 1, characterized in that, the compound having the formula $CF_{3-x}Cl_xCHClCHF_{2-y}Cl_y$ in step (a) is selected from the group consisting of $CCl_3CHClCHCl_2$, $CFCl_2CHClCHCl_2$, $CF_2ClCHClCHCl_2$, $CCl_3CHClCHFCl$ and $CFCl_2CHClCHFCl$.

3. The process for the preparation of 1,3,3,3-tetrafluoropropene according to claim 2, characterized in that, the compound having the formula $CF_{3-x}Cl_xCHClCHF_{2-y}Cl_y$ in step (a) is $CCl_3CHClCHCl_2$.

4. The process for the preparation of 1,3,3,3-tetrafluoropropene according to claim 1, characterized in that, the fluorination catalyst in step (a) is a Mn-A-B—C compound catalyst, wherein, A is a Group VIII element, B is a high-field-strength element, C is an alkaline-earth metal element, and the molar ratio of Mn, A, B and C is (0.3-2):(0.6-5):(0.1-1):(2-9).

5. The process for the preparation of 1,3,3,3-tetrafluoropropene according to claim 4, characterized in that, in the Mn-A-B—C compound catalyst in step (a), A is one of Ni, Fe and Co or a combination of two or more thereof, B is one of Zr, Y and La or a combination of two or more thereof, and C is one of Mg, Ca and Ba; and the molar ratio of Mn, A, B and C is (0.6-1):(2-4):(0.4-1):(4-7).

6. The process for the preparation of 1,3,3,3-tetrafluoropropene according to claim 4, characterized in that, the Mn-A-B—C compound catalyst in step (a) is Mn—Ni—Zr—Ca, wherein, the molar ratio of Mn, Ni, Zr and Ca is 0.6:3:0.4:6; the process for the preparation of the catalyst comprises the following steps: a mixed solution of soluble salts of the three metals Mn, Ni and Zr is reacted with a precipitant in proportion, the pH is controlled at 7.5 to 9.5, stirring, precipitating, filtering and drying are conducted, then an oxide, hydroxide or carbonate of Ca is homogeneously mixed therewith, and then staged calcination is performed at 200° C. to 500° C. under a condition of no less than three temperature gradients, and finally activation treatment is carried out with hydrogen fluoride at 200° C. to 380° C. to obtain the catalyst.

7. The process for the preparation of 1,3,3,3-tetrafluoropropene according to claim 1, characterized in that, the number n of serially-connected reactors in step (a) are two serially-connected reactors arranged in series in the flowing direction of the raw material and charged with the same catalyst, which have sequentially increased reaction temperatures.

8. The process for the preparation of 1,3,3,3-tetrafluoropropene according to claim 7, characterized in that, the reaction conditions of a primary reactor in the two serially-connected reactors in step (a) are as follows: the reaction temperature of the primary reactor is 200° C. to 240° C., the molar ratio of hydrogen fluoride to $CCl_3CHClCHCl_2$ is (5-20):1, and the reaction contact time is 0.5 to 20 seconds; and the reaction conditions of a secondary reactor are as follows: the reaction temperature of the secondary reactor is 280° C. to 320° C., the molar ratio of hydrogen fluoride to the organics in the primary reactor product is (10-20):1, and the reaction contact time is 5 to 30 seconds.

9. The process for the preparation of 1,3,3,3-tetrafluoropropene according to claim 1, characterized in that, the dechlorination catalyst in step (b) is a Cu—V—Mg—F catalyst, wherein, the molar ratio of Cu, V and Mg is (2-4):(1-2):(4-7); the reaction conditions of gas phase dechlorination are as follows: the reaction temperature is 200° C. to 320° C., the molar ratio of hydrogen to the total amount of 1,2,3-trichloro-1,1,3-trifluoropropane and 1,2-dichloro-1,1,3,3-tetrafluoropropane is (0-1):1, and the contact time is 1 to 30 seconds.

10. The process for the preparation of 1,3,3,3-tetrafluoropropene according to claim 1, characterized in that, the fluorination catalyst in step (c) is a Al—Co—Zn—F catalyst, wherein, the molar ratio of Al, Co and Zn is (6-8):(1-2):(1-2); the gas phase fluorination reaction conditions are as follows: the reaction temperature is 120° C. to 240° C., the molar ratio of hydrogen fluoride to the total amount of 3-chloro-1,3,3-trifluoropropene and 1,1,3,3-tetrafluoropropene is (5-20):1, and the contact time is 0.1 to 20 seconds.

11. The process for the preparation of 1,3,3,3-tetrafluoropropene according to claim 5, characterized in that, the Mn-A-B—C compound catalyst in step (a) is Mn—Ni—Zr—Ca, wherein, the molar ratio of Mn, Ni, Zr and Ca is 0.6:3:0.4:6; the process for the preparation of the catalyst comprises the following steps: a mixed solution of soluble salts of the three metals Mn, Ni and Zr is reacted with a precipitant in proportion, the pH is controlled at 7.5 to 9.5, stirring, precipitating, filtering and drying are conducted, then an oxide, hydroxide or carbonate of Ca is homogeneously mixed therewith, and then staged calcination is performed at 200° C. to 500° C. under a condition of no less than three temperature gradients, and finally activation treatment is carried out with hydrogen fluoride at 200° C. to 380° C. to obtain the catalyst.

* * * * *